(12) United States Patent
Kim et al.

(10) Patent No.: US 7,081,952 B2
(45) Date of Patent: Jul. 25, 2006

(54) METHOD AND APPARATUS FOR OBTAINING AN IMAGE USING A SELECTIVE COMBINATION OF WAVELENGTHS OF LIGHT

(75) Inventors: Kye-Weon Kim, Suwon (KR); Chung-Sam Jun, Suwon (KR); Hyun-Tae Kang, Yongin (KR)

(73) Assignee: Samsung Electronics Co., Ltd., Suwon (KR)

( * ) Notice: Subject to any disclaimer, the term of this patent is extended or adjusted under 35 U.S.C. 154(b) by 410 days.

(21) Appl. No.: 10/718,817

(22) Filed: Nov. 24, 2003

(65) Prior Publication Data
US 2004/0109157 A1 Jun. 10, 2004

(30) Foreign Application Priority Data
Nov. 23, 2002 (KR) ................. 10-2002-0073262

(51) Int. Cl.
*G01N 21/00* (2006.01)
(52) U.S. Cl. .................................. 356/237.1
(58) Field of Classification Search ............ None
See application file for complete search history.

(56) References Cited

U.S. PATENT DOCUMENTS 4,407,008 A * 9/1983 Schmidt et al. ............ 348/79
4,856,898 A * 8/1989 Becker-Ross et al. ...... 356/328
5,504,575 A 4/1996 Stafford ..................... 356/330
6,630,996 B1 * 10/2003 Rao et al. ................ 356/237.5
6,636,301 B1 * 10/2003 Kvamme et al. ........ 356/237.2
6,973,233 B1 * 12/2005 Tomita et al. ............. 385/31

FOREIGN PATENT DOCUMENTS

| JP | 2000097774 | 4/2000 |
| JP | 2000146838 | 5/2000 |

* cited by examiner

*Primary Examiner*—Hwa (Andrew) Lee
*Assistant Examiner*—Ali Allawi
(74) *Attorney, Agent, or Firm*—Lee & Morse, P.C.

(57) ABSTRACT

A method for obtaining an image using a selective combination of wavelengths of light includes dispersing a light in accordance with wavelength bands of the light using a dispersing member, irradiating the dispersed light onto an object to measure reflectivities of the light reflected from the object in accordance with the wavelength bands of the light, comparing reflectivity differences between an objective region and a peripheral region of the object, selecting wavelength bands having the reflectivity differences indicated as either positive values or negative values, adjusting the dispersing member to transmit only the light having the selected wavelength bands, passing light only having the selected wavelength bands through the dispersing member to irradiate the light that has passed through the dispersing member onto the object, taking photographs of the object using the irradiated light, and superposing the photographs of the object to obtain the image of the object.

12 Claims, 11 Drawing Sheets

//METHOD AND APPARATUS FOR OBTAINING AN IMAGE USING A SELECTIVE COMBINATION OF WAVELENGTHS OF LIGHT

BACKGROUND OF THE INVENTION

1. Field of the Invention

The present invention relates to a method and an apparatus for obtaining an image using a selective combination of light wavelengths. More particularly, the present invention relates to a method and an apparatus for obtaining an image using a selective combination of light wavelengths that can effectively obtain an image of an object, such as a stacked structure, using lights having selectively combined wavelength bands in accordance with the wavelength bands thereof.

2. Description of the Related Art

Generally, an apparatus for obtaining an image using light includes a light irradiation device for irradiating light onto an object and an imaging device like a camera for obtaining photographs of the object after the light is irradiated onto the object. The light irradiation device has a spectrometer for transmitting lights having desired wavelength bands according to a construction of the object.

Figure 1:
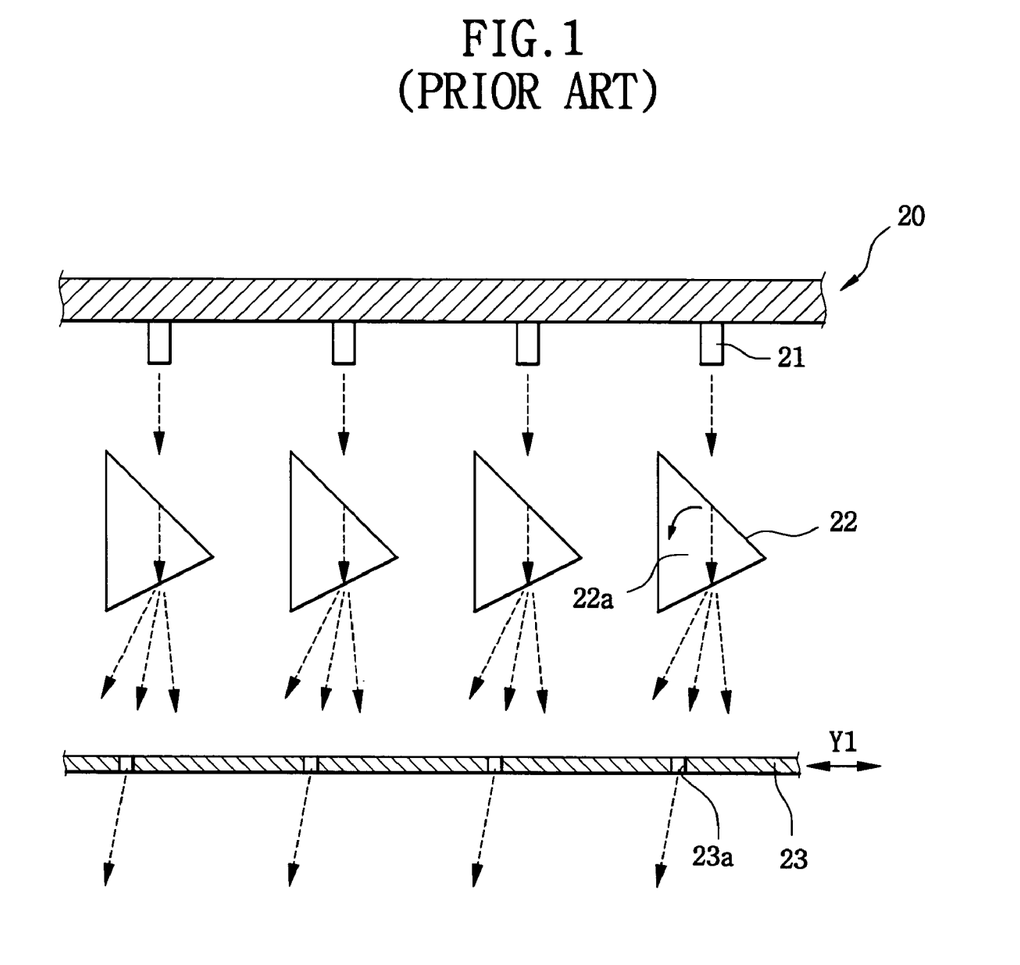
FIG. 1 illustrates a schematic cross-sectional view of a conventional light irradiation device of an apparatus for obtaining an image.

FIG. 1 illustrates a schematic cross-sectional view of a conventional light irradiation device.

Referring to FIG. 1, a light irradiation device 20 includes a light source 21, such as a white LED, for emitting white light, a micro prism 22 for dispersing the white light 22a along a dispersion direction Y1, and a barrier 23 including a slit 23a for transmitting the light having predetermined wavelength bands among all the dispersed light. The slit 23a moves along the dispersion direction Y1 in order to transmit the light having changed wavelength bands or a width of the slit 23a is varied to transmit the light having varied wavelength bands.

Figure 2:
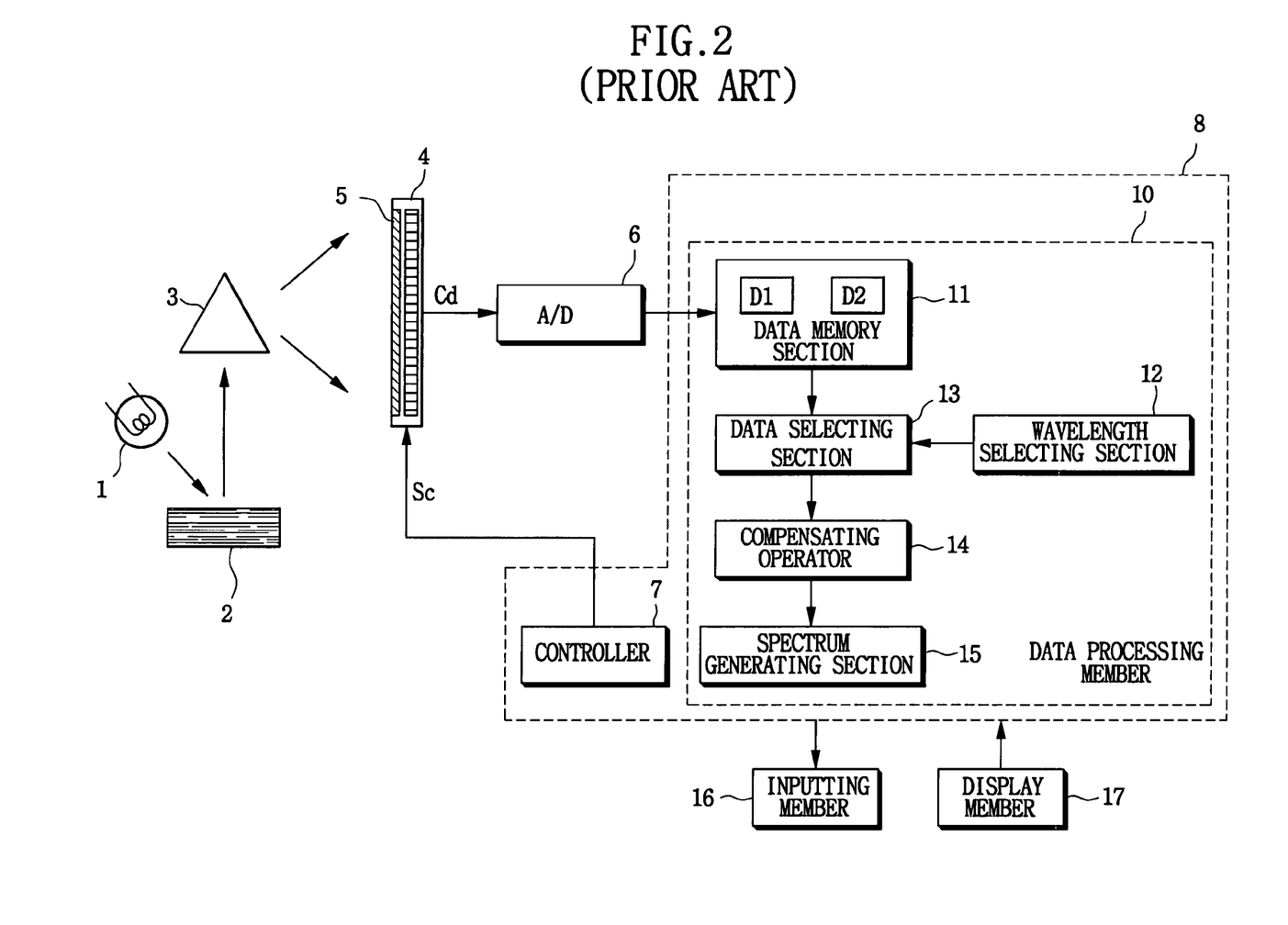
FIG. 2 illustrates a schematic cross-sectional view of a conventional spectrometer of an apparatus for obtaining an image.

FIG. 2 illustrates a schematic cross-sectional view of a conventional spectrometer.

Referring to FIG. 2, diffraction grids of a spectrometer 3 receive light reflected from a sample 2 after the light generated from a light source 1 is irradiated onto the sample 2. The spectrometer 3 disperses the light in a direction corresponding to wavelengths of the light. The dispersed light advances to a charge coupled device (CCD) line sensor 4 wherein minute light receiving devices are arranged. The CCD line sensor 4 includes a shutter 5 for electronically shielding light receiving faces thereof. A controller 7 generates shutter opening and closing signals Sc for controlling an opening period of the shutter 5 to adjust an amount of light received on the light receiving faces of the minute light receiving devices of the CCD line sensor 4.

An output signal Cd of the CCD line sensor 4 is received in a data processing member 10 through an A/D converter 6. The data processing member 10 includes a data memory section 11, a wavelength selecting section 12, a data selecting section 13, a compensating operator 14 and a spectrum generating section 15. The spectrometer 3 further includes an inputting member 16 and a display member 17 electrically connected to the data processing member 10.

Figure 3:
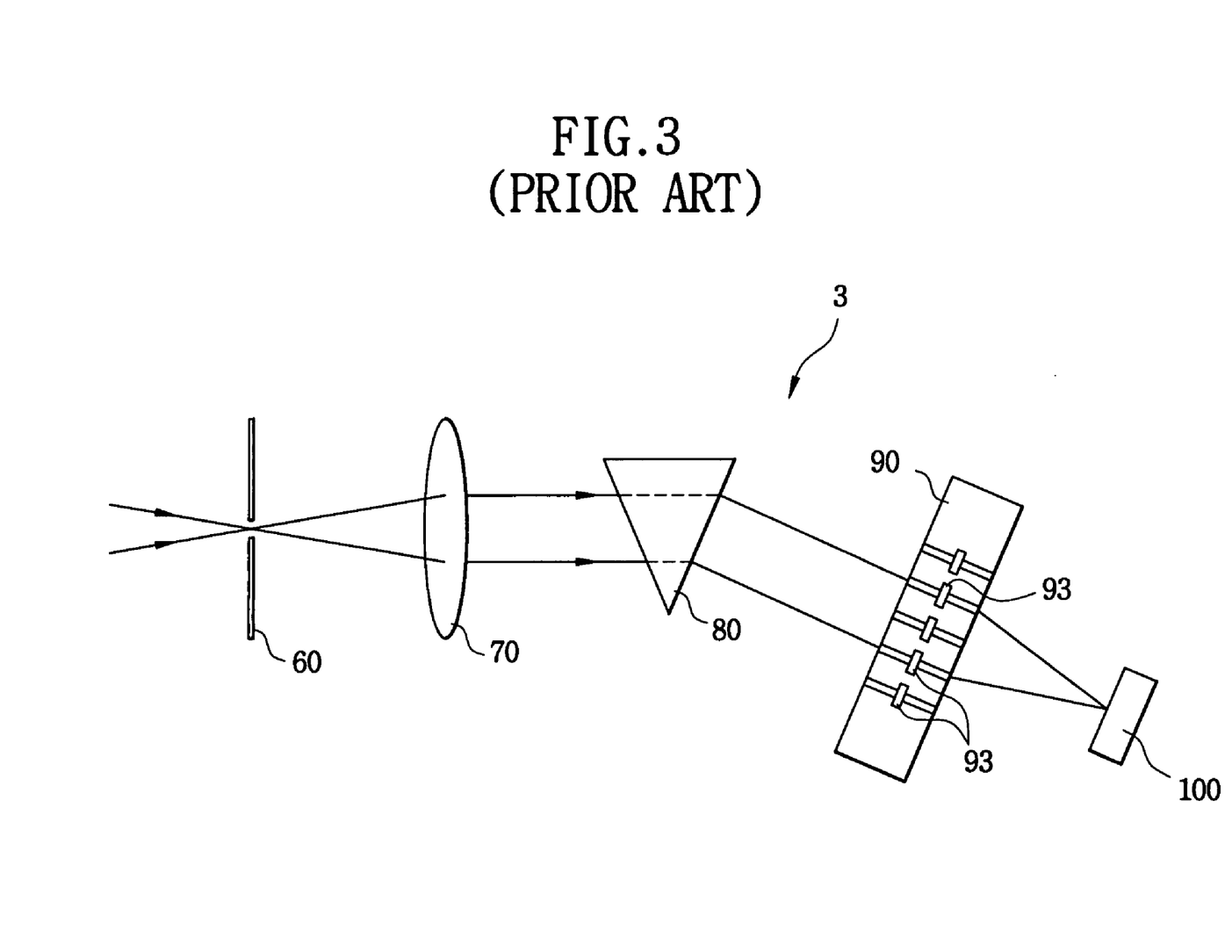
FIG. 3 illustrates a schematic cross-sectional view of another conventional spectrometer of an apparatus for obtaining an image.

FIG. 3 illustrates a schematic cross-sectional view of another conventional spectrometer.

Referring to FIG. 3, after light has passed through a slit 60, the light is converted into parallel light by a collimator 70. The parallel light is dispersed while the light passes through a prism 80. The dispersed light passes through a shutter 93 of a light modulator 90, and is incident upon a detecting member 100.

The above-mentioned apparatus for obtaining an image may be utilized in various fields. For example, the apparatus for obtaining an image may be employed to obtain images of patterns stacked on a wafer. The apparatus for obtaining an image primarily includes a light source emitting white light. However, a contrast ratio between images of the patterns obtained using the white light may be exceedingly low when a step between patterns formed on a wafer becomes minute as a planarization process is performed on the patterns on the wafer. More specifically, when the white light, which includes all wavelength bands, is irradiated onto the patterns to obtain the images of the patterns, reflection intensities of the light reflected from the patterns may be very low at all of the wavelength bands of the reflected light because of the minute step between the patterns. Hence, the images of the patterns may be hardly recognized.

In view of the above-mentioned problem, an apparatus including color filters disposed at light receiving portions thereof in order to select one filter wherein a wavelength band has a high contrast ratio among all of the wavelength bands of white light incident upon the color filters has been suggested. However, the selected wavelength band of the light may be fixed because one of the color filters should correspond to a predetermined wavelength band of the light. A contrast ratio between images of patterns generally depends on structures of the patterns and adjacent films. The wavelength band having the high contrast ratio may be varied according to this structure. Therefore, an image having a high contrast ratio may not be obtained using the color filters corresponding to the fixed wavelength bands.

Additionally, a method for obtaining an image by amplifying an image signal as a noise is reduced by taking an average of data numerals of obtained images after several images of an object are obtained has been suggested. However, this method may have a limitation in that the image signal may not be amplified to a certain degree. Thus, an image having a highest contrast ratio may not be obtained and a time for obtaining the image may be greatly increased because several images must be obtained.

SUMMARY OF THE INVENTION

It is a first feature of the present invention to provide a method for obtaining an image using a wavelength band of light that generates the highest contrast ratio after the wavelength band is changeably selected.

It is a second feature of the present invention to provide an apparatus for obtaining an image using a wavelength band of light that generates the highest contrast ratio after the wavelength band is changeably selected.

In accordance with an embodiment of the present invention, a method for obtaining an image using a selective combination of wavelengths of light, includes dispersing a light in accordance with wavelength bands of the light using a dispersing member, irradiating the dispersed light onto an object to measure reflectivities of the light reflected from the object in accordance with the wavelength bands of the light, comparing reflectivity differences between an objective region of the object and a peripheral region of the object, selecting wavelength bands having the reflectivity differences indicated as either positive values or negative values, adjusting the dispersing member to transmit only the light having the selected wavelength bands, passing light only having the selected wavelength bands through the dispersing member to irradiate the light that has passed through the dispersing member onto the object, taking photographs of the object using the irradiated light, and superposing the photographs of the object to obtain the image of the object.

The dispersing member may be adjusted by controlling rotation angles of a rotatable prism for dispersing the light. In that case, the method may further include transmitting the light through a single slit after the light passes through the rotatable prism rotated by the controlled rotation angles and condensing the light that has passed through the single slit.

Alternately, the dispersing member may be adjusted by controlling positions of opened portions of an openable slit for transmitting the light in accordance with the wavelength bands of the light. In that case, the method may further include dispersing the light using a prism before transmitting the light through the openable slit and condensing the light that has passed through the openable slit.

In accordance with another embodiment of the present invention, an apparatus for obtaining an image using a selective combination of wavelengths of light includes a light source for generating a light, dispersing means for dispersing the light to form dispersed light, measuring means for measuring reflectivities of the reflected light in accordance with wavelength bands of the light after the light is irradiated onto a object, comparing means for comparing reflectivity differences between an object region of the object and a peripheral region of the object, selecting means for selecting wavelength bands having the reflectivity differences indicated as either positive values or negative values, adjusting means for adjusting the dispersing means to disperse light having the selected wavelength bands only, imaging means for taking photographs of the object using the dispersed light, and superposing means for superposing the photographs of the object to produce an image of the object.

The dispersing means may include a rotatable prism for dispersing the light generated from the light source and a single slit for transmitting the dispersed light. Alternately, the dispersing means may include a prism for dispersing the light generated from the light source and an openable slit for selectively transmitting the dispersed light.

According to the present invention, reflectivity differences between the object region and the peripheral region of an object are measured after light is irradiated onto the object. Then, the image of the object, for example, a structure on a wafer, is obtained using the light having wavelength bands of positive or negative reflectivity differences. Therefore, the image of the object can have a high contrast ratio. As a result, a structure of the object such as a wafer, and more particularly a stacked structure of the object, may be apparently obtained.

BRIEF DESCRIPTION OF THE DRAWINGS

The above and other features and advantages of the present invention will become more apparent to those of ordinary skill in the art by describing in detail exemplary embodiments thereof with reference to the accompanying drawings in which.

DETAILED DESCRIPTION OF THE INVENTION

Korean Patent Application 2003-73262, filed on Nov. 23, 2003, and entitled: "Method and Apparatus for Obtaining an Image Using a Selective Combination of Wavelengths of Light," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. Like reference numerals refer to like elements throughout.

FIRST EMBODIMENT

Figure 4:
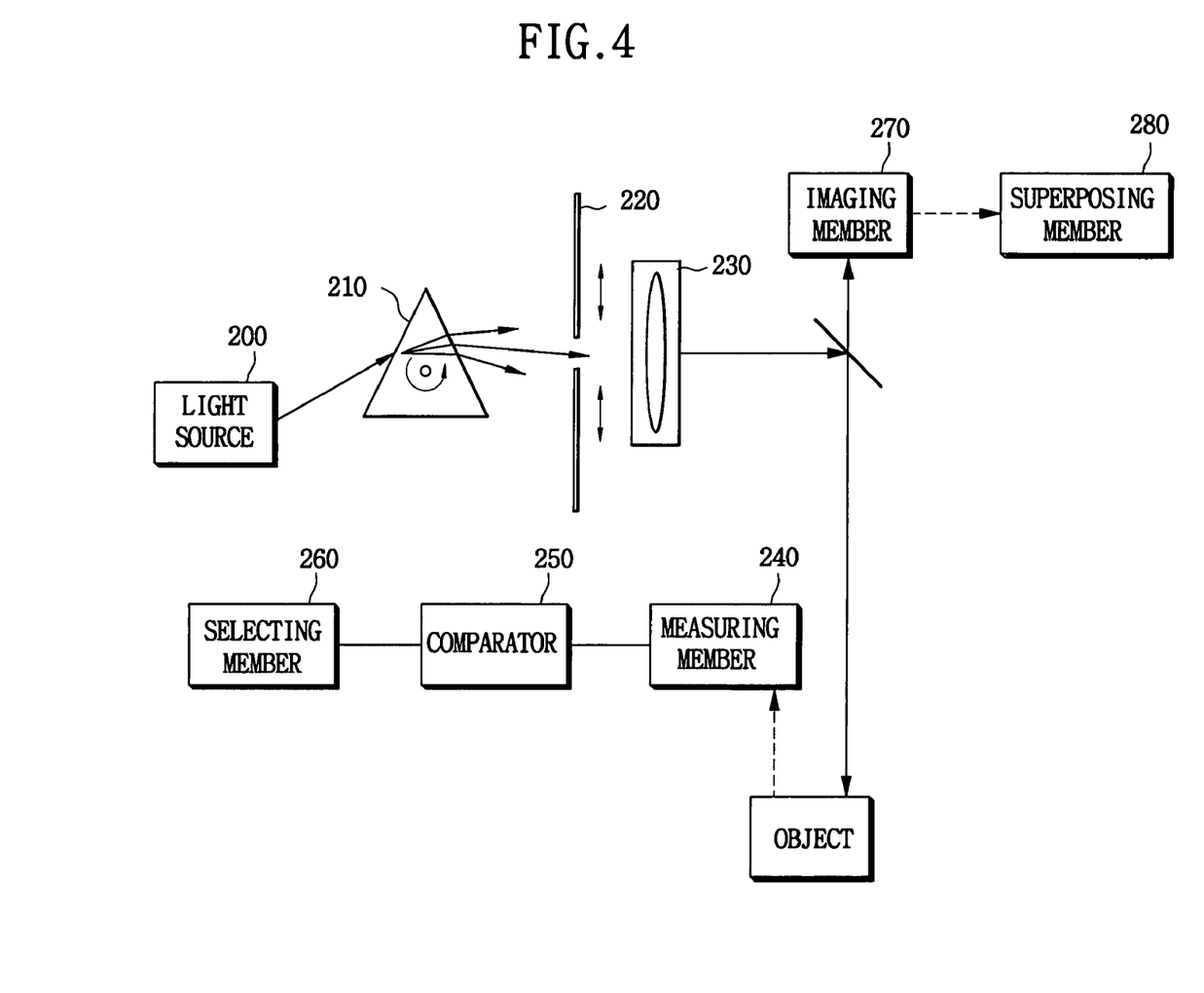
FIG. 4 illustrates a schematic cross-sectional view of an apparatus for obtaining an image according to a first embodiment of the present invention.
Figure 5:
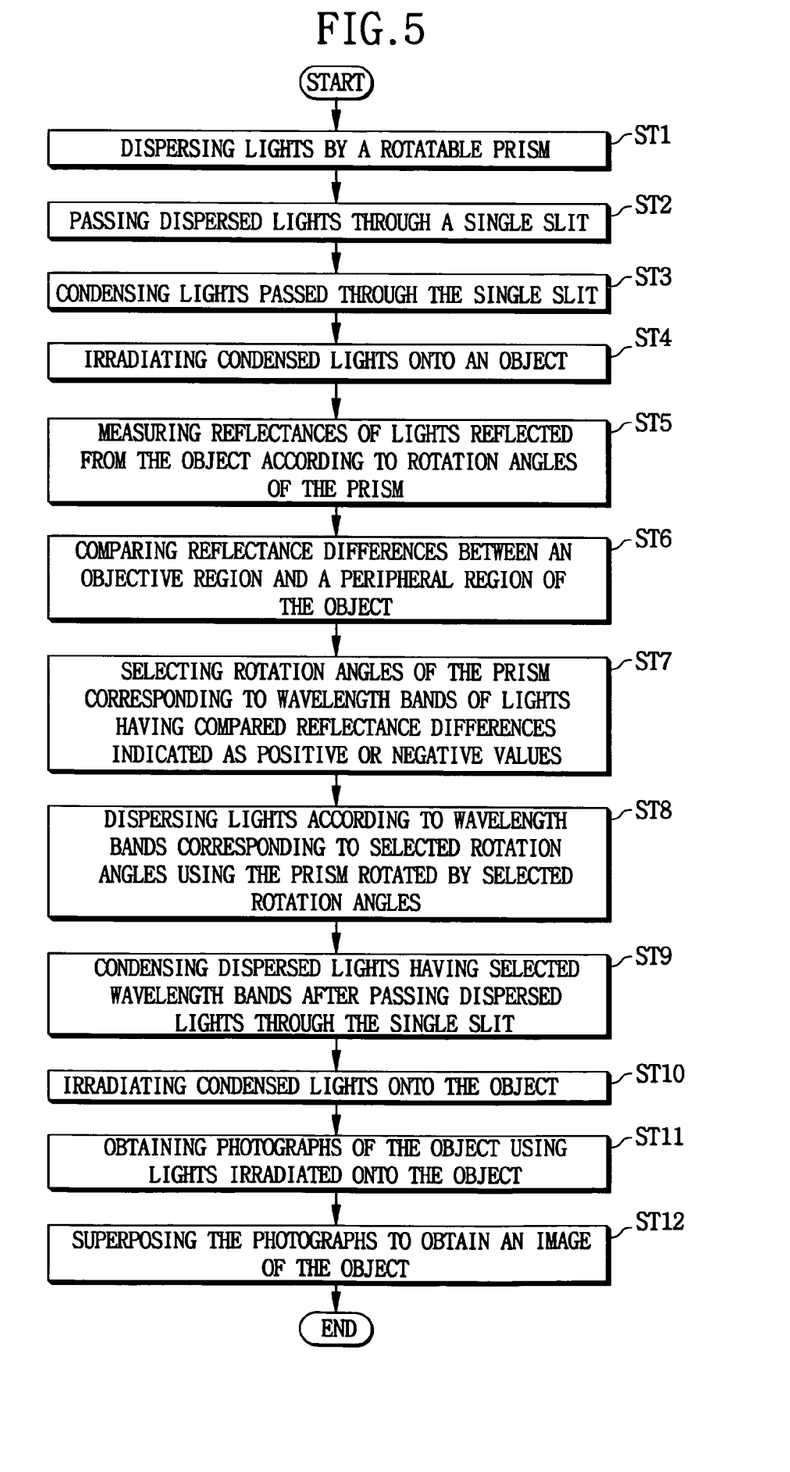
FIG. 5 is a flow chart illustrating a method for obtaining an image using the apparatus in FIG. 4.

FIG. 4 illustrates a schematic cross-sectional view of an apparatus for obtaining an image according to a first embodiment of the present invention. FIG. 5 is a flow chart illustrating a method for obtaining an image using the apparatus in FIG. 4.

Referring to FIG. 4, light generated from a light source 200 is incident upon a rotatable prism 210. The rotatable prism 210 rotates by predetermined angles so that the light incident upon the rotatable 210 is dispersed in accordance with wavelength bands thereof.

The dispersed light pass through a single slit 220. The light that passes through the single slit 220 is condensed using a condenser 230. Then, the condensed light is irradiated onto an object.

The light is reflected from the object and measured using a measuring member 240. The measuring member 240 measures reflectivity of the light in accordance with the wavelength bands of the light. A comparator 250 compares an objective region of the object, which is from where an image will be obtained, with a peripheral region of the object, which surrounds the objective region. More specifically, the comparator 250 compares the reflectivity of the objective region with the reflectivity of the peripheral region. Then, the comparator 250 measures reflectivity differences between the objective region and the peripheral region. A selecting member 260 selects the wavelength bands of the light corresponding to the reflectivity differences indicated as positive (+) values or negative (−) values. Because the selected wavelength bands can correspond to rotation angles of the rotatable prism 210, selections of the wavelength bands of the light means that the selection member 260 matches selections of the rotation angels of the rotatable prism 210.

The rotatable prism 210 is adjusted to rotate by the selected rotation angles. In this case, light is repeatedly irradiated onto the adjusted rotatable prism 210 and the light having the selected wavelength bands passes through the single slit 220 to be condensed by the condenser 230. The condensed light is repeatedly irradiated onto the object. An imaging member 270, such as a charge coupled device (CCD), takes photographs of the object. The photographs of the object are superposed using a superposing member 280 so that an image of the object having the highest contrast ratio can be obtained.

Hereinafter, a method for obtaining an image using the apparatus in FIG. 4 will be described with reference to FIG. 5.

Referring to FIG. 5, in step ST1, the light generated from the light source 200 is irradiated onto the rotatable prism 210 that is rotated by predetermined angles, thereby dispersing the light in accordance with wavelength bands thereof.

In step ST2, the dispersed light passes through the single slit 220. Then, in step ST3, the light that has passed through the single slit 220 is condensed using the condenser 230. In step ST4, the condensed light is irradiated onto the object.

In step ST5, reflectivity of the light reflected from the object is measured using the measuring member 240 in accordance with the wavelength bands of the light. The wavelength bands of the reflected light correspond to rotation angles of the prism 210 so that the reflectivity of the light according to the wavelength bands also correspond to the rotation angles of the rotatable prism 210.

In step ST6, reflectivity differences between an objective region of the object and a peripheral region of the object are compared and measured using the comparator 250. In step ST7, the rotation angles of the rotatable prism 210, which correspond to the reflectivity differences indicated as positive or negative values, are selected using the selecting member 260. More specifically, the selecting member 260 selects some wavelength bands having the reflectivity differences of the positive values and other wavelength bands having the reflectivity differences of the negative values.

In step ST8, the light is repeatedly incident upon the rotatable prism 210 rotated by the rotation angles selected by the selection member 260 so that the light is dispersed in accordance with wavelength bands thereof corresponding to the selected rotation angles.

After the dispersed light having the selected wavelength bands passes through the single slit 220, in step ST9, the light is condensed using the condenser 230. In step ST10, the condensed light is irradiated onto the object, and then, in step ST11, photographs of the object are obtained using the imaging member 270. Finally, in step ST12, the obtained photographs of the object are superposed to obtain an image of the object.

According to the first embodiment, the obtained image of the object is able to have a very high contrast ratio because the image of the object is obtained using light having wavelength bands having the highest reflection intensities. As a result, a structure of the object, particularly, a stacked structure of the object, can be more apparently obtained.

SECOND EMBODIMENT

Figure 6:
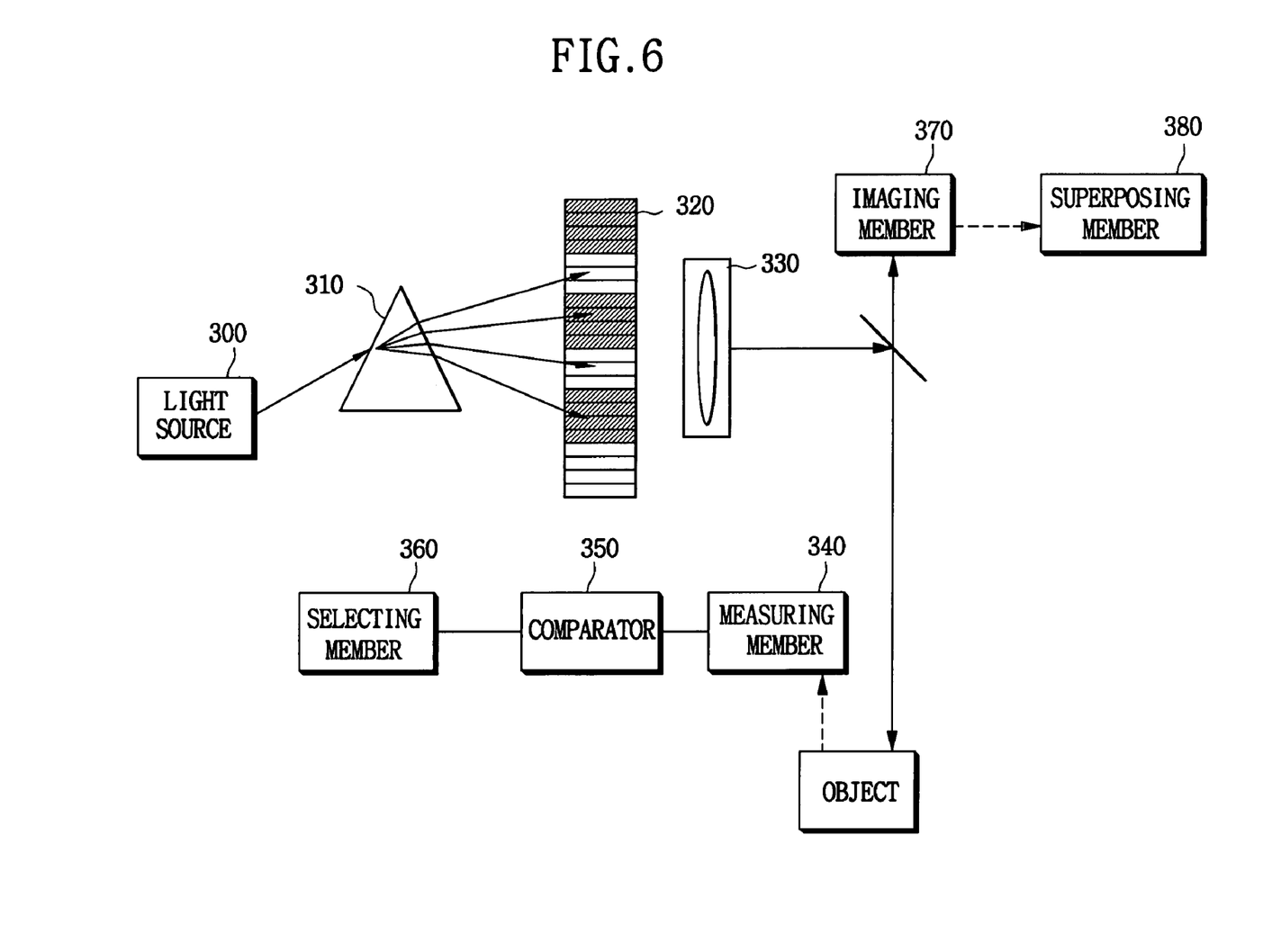
FIG. 6 illustrates a schematic cross-sectional view of an apparatus for obtaining an image according to a second embodiment of the present invention.
Figure 7:
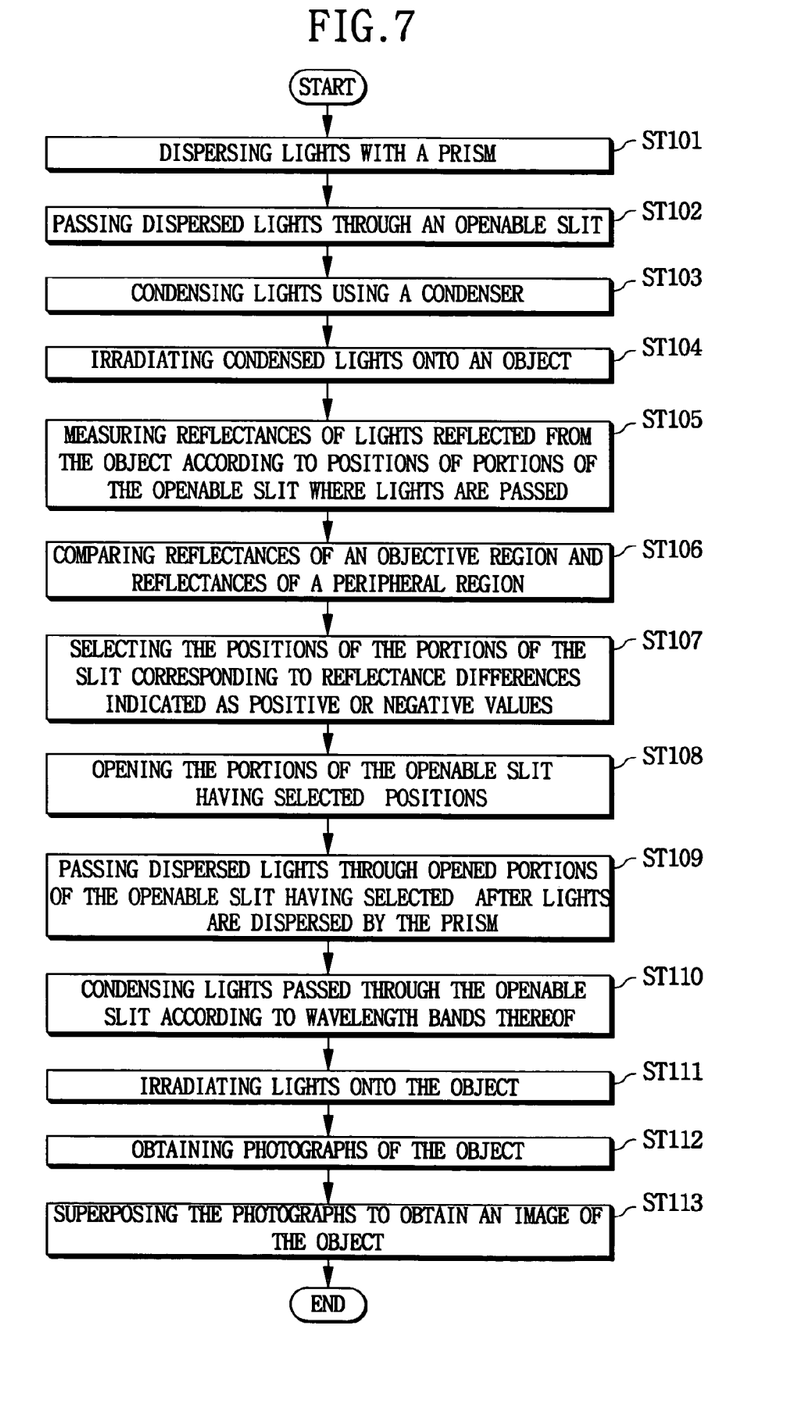
FIG. 7 is a flow chart illustrating a method for obtaining an image using the apparatus in FIG. 6.

FIG. 6 illustrates a schematic cross-sectional view of an apparatus for obtaining an image according to a second embodiment of the present invention. FIG. 7 is a flow chart illustrating a method for obtaining an image using the apparatus as shown in FIG. 6.

Referring to FIG. 6, light generated from a light source 300 is incident upon a prism 310. The light incident upon the prism 310 is dispersed in accordance with wavelength bands thereof.

The dispersed light passes through an openable slit 320. Portions of the openable slit 320 are opened so that all the light passes through the openable slit 320. The light that has passed through the openable slit 320 is condensed using a condenser 330. The condensed light is irradiated onto an object.

The light is reflected from the object and measured using a measuring member 340. The measuring member 340 measures reflectivity of the light in accordance with the wavelength bands of the light. A comparator 350 compares an objective region of the object, which is from where an image will be obtained, with a peripheral region of the object, which surrounds the objective region. More specifically, the comparator 350 compares the reflectivity of the objective region with the reflectivity of the peripheral region. Then, the comparator 350 measures reflectivity differences between the objective region and the peripheral region. A selecting member 360 selects the wavelength bands of the light corresponding to the reflectivity differences indicated as positive values or negative values. The selected wavelength bands of the light correspond to portions of the openable slit 320 that can be opened. Thus, the portions of the openable slit 320 are also selected by the selecting member 360.

Selected portions of the openable slit 320 are opened while other portions of the slit 320 are closed. After the light is dispersed through the prism 310, the dispersed light passes through the opened portions of the openable slit 320. Hence, only light having predetermined wavelength bands pass through the opened portions of the slit 320. The light having the predetermined wavelength bands is condensed using the condenser 330. The condensed light is irradiated onto the object, and an imaging member 370 including a CCD camera takes photographs of the object. The photographs of the object are superposed using a superposing member 380, thereby obtaining an image of the object.

Hereinafter, a method for obtaining an image using the apparatus in FIG. 6 will be described.

Referring to FIG. 7, in step ST101, light generated from the light source 300 is irradiated onto the prism 310, thereby dispersing the light in accordance with wavelength bands thereof. In step ST102, the dispersed light passes through the opened portions of the openable slit 320.

Then, in step ST103, the light that has passed through the openable slit 320 is condensed using the condenser 330. In step ST104, the condensed light is irradiated onto the object.

In step ST105, reflectivities of the light reflected from the object are measured using the measuring member 340 in accordance with positions of the opened portion of the openable slit 320 through which the light passes. More specifically, the reflectivities of the light are measured according to the wavelength bands of the light because the wavelength bands of the light correspond to the positions of the opened portions of the openable slit 320. Thus, intensities of the wavelength bands of the reflected light correspond to those of the light that passes through the openable slit 320.

In step ST106, reflectivity differences between an objective region of the object and a peripheral region of the object are compared and measured using the comparator 350. In step ST107, the positions of the opened portions of the openable slit 320, which correspond to the reflectivity differences indicated as positive or negative values, are selected using the selecting member 360. That is, the selecting member 360 selects some wavelength bands of the reflected light having the reflectivity differences of the positive values and other wavelength bands of the reflected light having the reflectivity differences of the negative values.

In step ST108, portions of the openable slit 320 having the selected positions are opened. The light is repeatedly incident upon the prism 310 so that the light is dispersed in accordance with the wavelength bands thereof that correspond to the selected positions of the openable slit 320. Then, in step ST109, the dispersed light passes through the opened portions of the openable slit 320 corresponding to the selected positions. In this case, the dispersed light can pass through the opened portions of the openable slit 320 corresponding to the selected wavelength bands of the light. Hence, only light having the selected wavelength bands can pass through the openable slit 320.

In step ST110, the light is condensed using the condenser 330. After the condensed light is irradiated onto the object in step ST111, photographs of the object are obtained using the imaging member 370 in step ST112. Finally, in step ST113, the obtained photographs of the object are superposed to obtain an image of the object.

In the embodiments of the present invention, the method for obtaining the image of the object may not be repeatedly performed for all regions of the object. When wavelength bands of the light having the highest contrast ratios are selected, the image of the object can be obtained using the light having the selected wavelength bands in accordance with an adjustment of the rotatable prism 210 or the openable slit 320. That is, a process for selecting the wavelength bands of the light is executed only once concerning one object or several objects treated by identical processes.

Hereinafter, an experiment embodying the present invention will be described.

Figure 8:
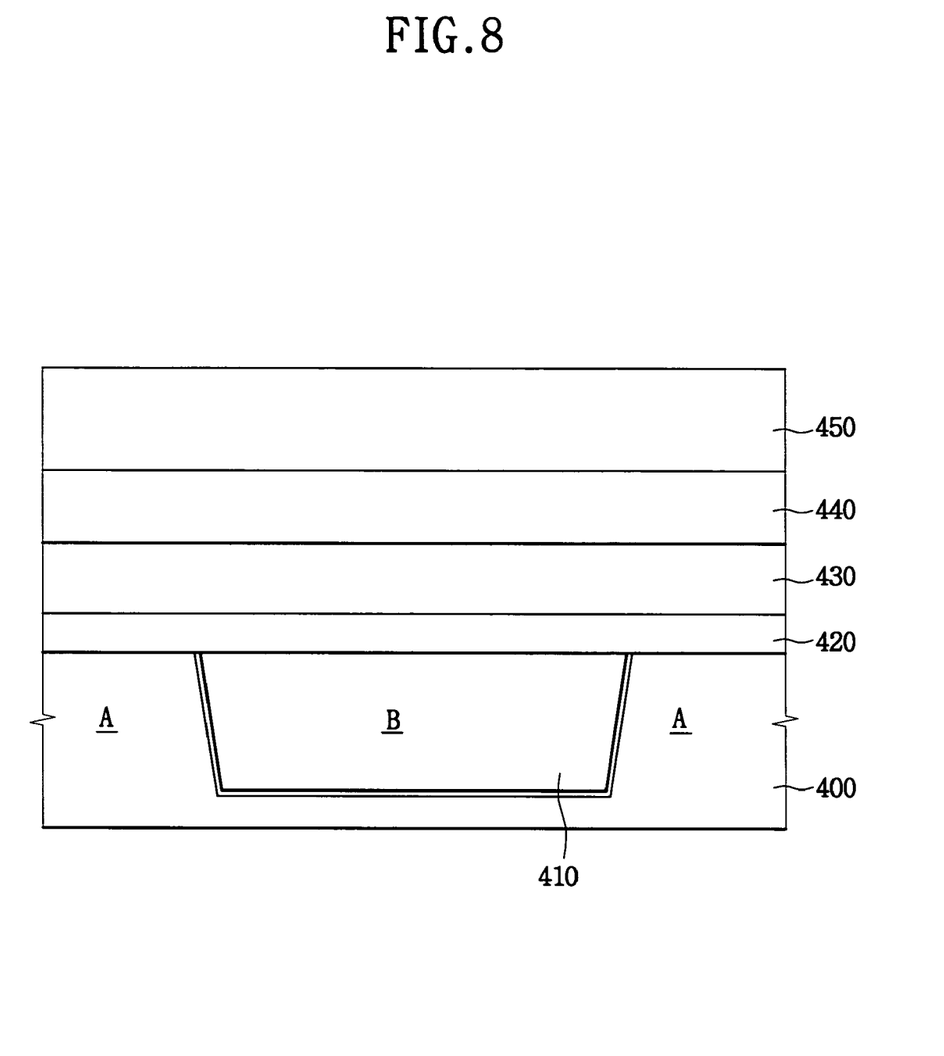
FIG. 8 illustrates a schematic cross-sectional view of a wafer having a stacked structure according to the present invention.

FIG. 8 illustrates a schematic cross-sectional view of a wafer including a stacked structure that will be imaged in accordance with the present invention.

Referring to FIG. 8, after an oxide film 410 was formed on a first silicon wafer 400, the oxide film 410 was polished using a chemical mechanical polishing (CMP) process. When the oxide film 410 was formed in a central region of the first wafer 400, the first wafer 400 was divided into a first region A and a second region B. The oxide film 410 was positioned in the second region B enclosed by the first region A.

A polysilicon film 420, a tungsten silicide film 430, a silicon nitride film 440 and a photoresist film 450 were successively formed on the first wafer 400 including the oxide film 410.

Meanwhile, a second wafer (not shown) was prepared to have a same structure as in the first wafer 400 except that the oxide film 410 of the second wafer had a different thickness from that of the first wafer 400.

Figure 9:
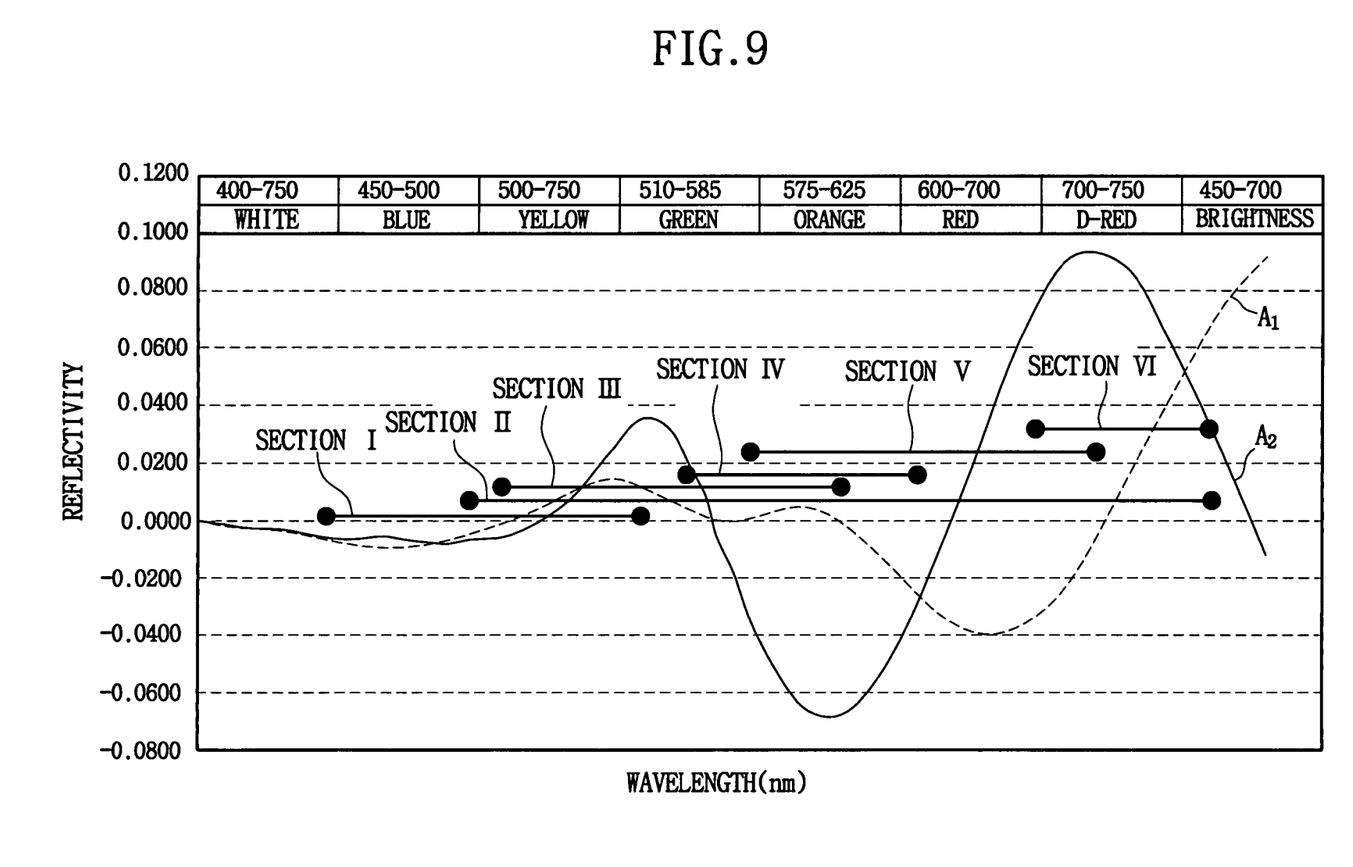
FIG. 9 is a graph showing a variation of reflectivity of a wafer relative to a wavelength according to the present invention.

FIG. 9 is a graph showing a variation of reflectivities of wafers relative to wavelengths obtained in accordance with the present invention. In FIG. 9, a horizontal axis indicates a wavelength of light and a vertical axis represents a reflectivity of a wafer. Reflectivities of the first wafer 400 are indicated as a first curve $A_1$ and reflectivities of the second wafer are represented as a second curve $A_2$. A first section I corresponds to wavelength bands of blue light, a second section II meets wavelength bands of yellow light, and a third section III falls under wavelength bands of green light. Additionally, a fourth section IV, a fifth section V and a sixth section VI correspond to wavelength bands of orange light, wavelength bands of red light and wavelength bands of deep red (D-red) light, respectively.

As shown in FIG. 9, after light is irradiated onto the first wafer 400 and onto the second wafer, reflectivities of the light reflected from the first wafer 400 and the second wafer were measured. Reflectivity differences between the first wafer 400 and the second wafer were considerably large in accordance with wavelength bands of the light. When the white light including all the wavelength bands of the light was used for obtaining images of the wafers as a conventional method for obtaining an image, the images may have poor contrast ratios because positive reflectivities may be compensated with negative reflectivities. Thus, stacked structures formed on the wafers may be hardly discerned using the conventional method for obtaining the image of the wafer.

Figure 10:
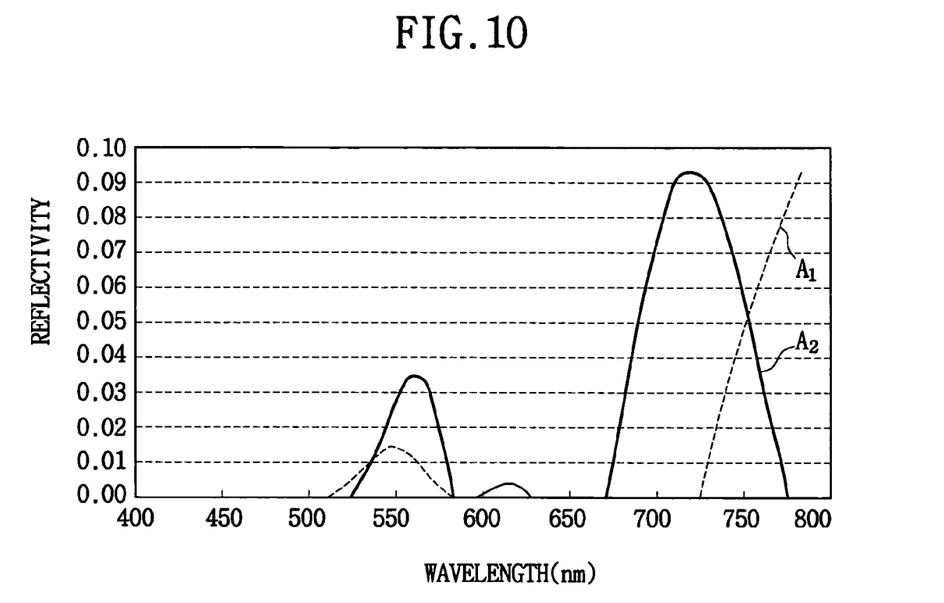
FIG. 10 is a graph showing positive values of reflectivity differences of the wafers in FIG. 9.
Figure 11:
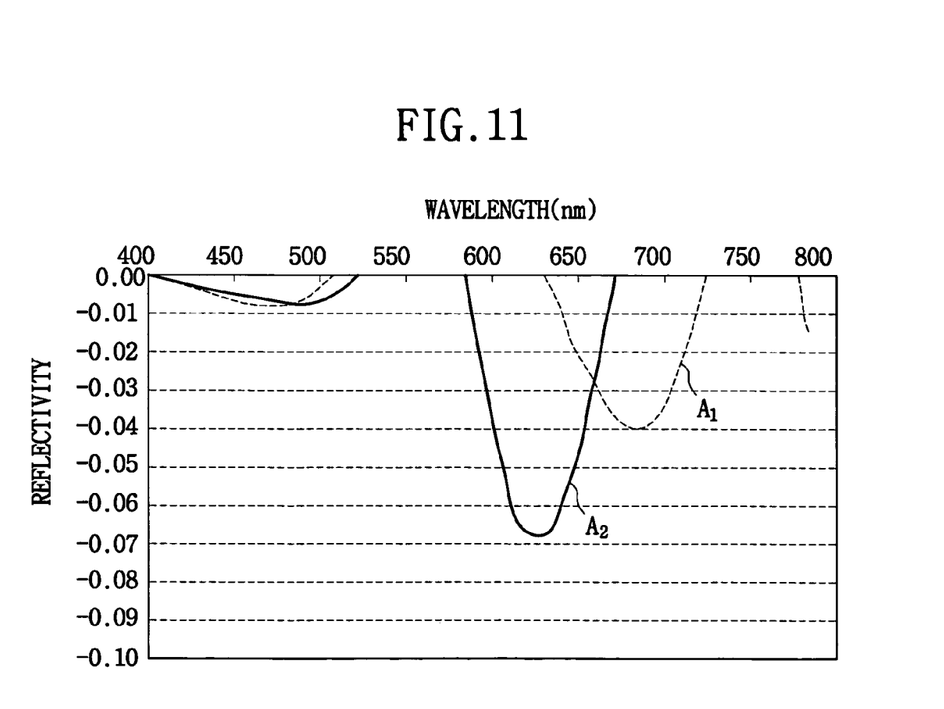
FIG. 11 is a graph showing negative values of reflectivity differences of the wafers in FIG. 9.

FIG. 10 is a graph showing positive values of the reflectivity differences of the wafers in FIG. 9. FIG. 11 is a graph showing negative values of the reflectivity differences of the wafers in FIG. 9. In FIGS. 10 and 11, the reflectivity differences of the first wafer 400 are indicated as a first curve $A_1$ and the reflectivity differences of the second wafer are represented as a second curve $A_2$.

To overcome the above-mentioned problem, according to the present experiment, reflectivity differences between the first wafer 400 and the second wafer were divided into positive values and negative values as shown in FIGS. 10 and 11, respectively.

Table 1 shows the results in FIGS. 10 and 11 in accordance with the wavelength bands of the light after comparison with white light.

TABLE 1

| wavelength band (nm) | Color | Reflectivities of the first wafer | Reflectivities of the second wafer |
| --- | --- | --- | --- |
| 400–750 | White | 0.639 | 2.319 |
| 450–500 | Blue | −0.030 | −0.280 |
| 500–750 | Yellow | −0.670 | 2.375 |
| 510–585 | Green | 0.466 | 0.947 |
| 575–625 | Orange | 0.085 | −1.546 |
| 600–700 | Red | −1.544 | −1.520 |
| 700–750 | D-red | 0.379 | 3.381 |
| +contrasted wavelength band | +contrasted wavelength | 2.96 | 5.85 |

Figure 12:
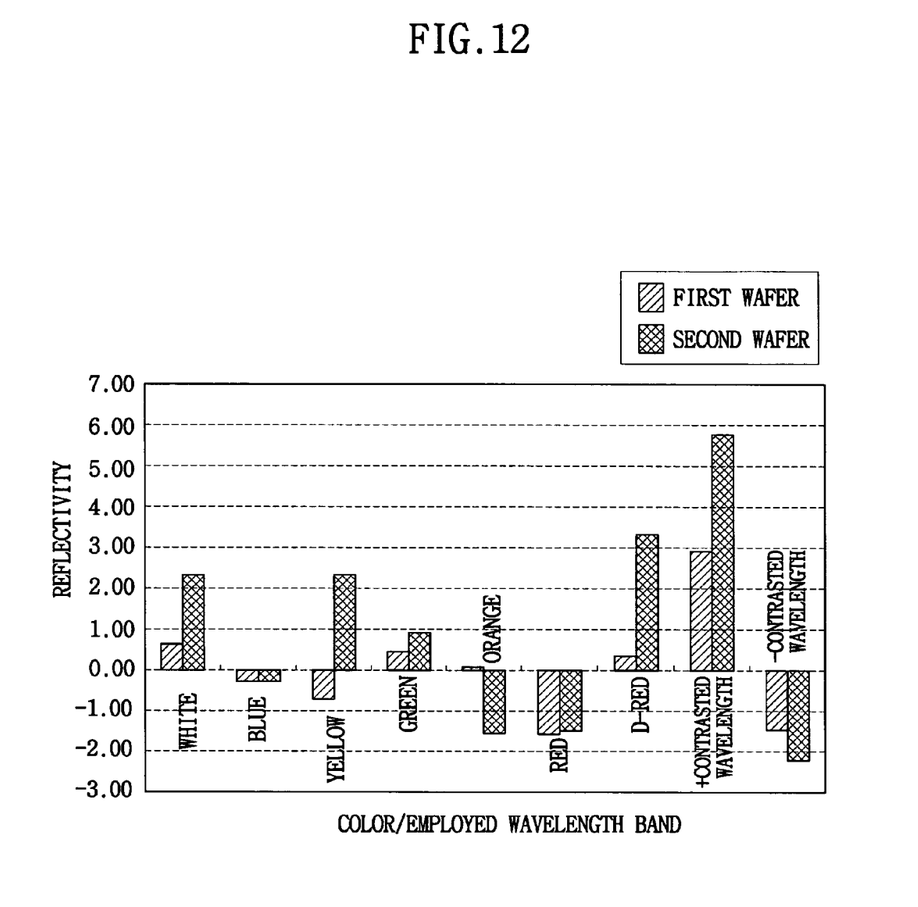
FIG. 12 is a graph showing reflectivity differences between a first wafer and a second wafer.

FIG. 12 is a graph illustrating results shown in Table 1.

Referring to Table 1 and FIG. 12, when the white light including all the wavelength bands was used, the reflectivity difference of the first wafer 400 was about 0.639. On the contrary, when the light having the wavelength bands of positive (+) reflectivity differences was used, the reflectivity difference of the first wafer 400 was about 2.96. Thus, the reflectivity difference of the first wafer 400 was significantly increased.

The reflectivity difference of the second wafer was about 2.139 when the white light including all the wavelength bands was used. Alternatively, when light having the wavelength bands of positive (+) reflectivity differences was used, the reflectivity difference of the second wafer was about 5.85. Hence, reflective difference of the second wafer was more than twice increased.

According to the present invention, an image having a high contrast ratio can be obtained when the light having the wavelength bands of positive (+) or negative (−) reflectivity differences were used instead of the white light including all the wavelength bands.

Table 2 shows optimum wavelengths bands of the first and second wafers selected in accordance with the present experiment.

TABLE 2

| contrasted images | Object | wavelength used (nm) | | |
|---|---|---|---|---|
| +contrasted wavelength | the first wafer | 515–625 | 725–800 | |
| | the second wafer | 530–580 | 670–775 | |
| −contrasted wavelength | the first wafer | 400–500 | 630–725 | |
| | the second wafer | 400–500 | 585–670 | 776–800 |

As shown in Table 2, an image of the first wafer 400 having a high contrast ratio could be obtained by superposing two photographs taken using the light of wavelength bands of about 515 nm to 625 nm and about 725 nm to 800 nm corresponding to the positive reflectivity differences or by superposing two photographs taken using the light of wavelength bands of about 400 nm to 500 nm and about 630 nm to 725 nm corresponding to the negative reflectivity differences.

In addition, an image of the second wafer having a high contrast ratio could be obtained by superposing two photographs taken using the light of wavelength bands of about 530 nm to 580 nm and about 670 nm to 775 nm corresponding to the positive reflectivity differences or by superposing three photographs taken using the light of wavelength bands of about 400 nm to 500 nm, about 585 nm to 670 nm and about 776 nm to 800 nm corresponding to the negative reflectivity differences.

According to the present invention, reflectivity differences between an object region and a peripheral region of an object are measured after light is irradiated onto the object. Then, an image of the object, for example, a structure on a wafer, is obtained by using the light having wavelength bands of positive or negative reflectivity differences. Therefore, the image of the object can have a high contrast ratio. As a result, a structure of the object like a wafer, particularly, a stacked structure of the object, can be apparently obtained.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method for obtaining an image using a selective combination of wavelengths of light, comprising:
   dispersing a light in accordance with wavelength bands of the light using a dispersing member;
   irradiating the dispersed light onto an object to measure reflectivities of the light reflected from the object in accordance with the wavelength bands of the light;
   comparing reflectivity differences between an objective region of the object and a peripheral region of the object;
   selecting wavelength bands having the reflectivity differences indicated as either positive values or negative values;
   adjusting the dispersing member to transmit only the light having the selected wavelength bands;
   passing light only having the selected wavelength bands through the dispersing member to irradiate the light that has passed through the dispersing member onto the object;
   taking photographs of the object using the irradiated light; and
   superposing the photographs of the object to obtain the image of the object.

2. The method as claimed in claim 1, wherein the dispersing member is adjusted by controlling rotation angles of a rotatable prism for dispersing the light.

3. The method as claimed in claim 2, further comprising:
   transmitting the light through a single slit after the light passes through the rotatable prism rotated by the controlled rotation angles.

4. The method as claimed in claim 3, further comprising:
   condensing the light that has passed through the single slit.

5. The method as claimed in claim 1, wherein the dispersing member is adjusted by controlling positions of opened portions of an openable slit for transmitting the light in accordance with the wavelength bands of the light.

6. The method as claimed in claim 5, further comprising:
   dispersing the light using a prism before transmitting the light through the openable slit.

7. The method as claimed in claim 6, further comprising:
   condensing the light that has passed through the openable slit.

8. A method for obtaining an image using a selective combination of wavelengths of light, comprising:
   dispersing a light using a rotatable prism;
   transmitting the dispersed light through a slit;
   condensing the light that has passed through the slit;
   irradiating the condensed light onto an object to measure reflectivities of the light reflected from the object in accordance with rotation angles of the rotatable prism;
   comparing reflectivity differences between an objective region of the object and a peripheral region of the object;
   selecting the rotation angles of the rotatable prism corresponding to the reflectivity differences indicated as either positive values or negative values;
   transmitting the light through the rotatable prism rotated by the selected rotation angles to disperse the light in accordance with wavelength bands corresponding to the selected rotation angles;
   transmitting the light dispersed in accordance with the wavelength bands through the slit to condense the light dispersed in accordance with the wavelength bands;
   irradiating the condensed light on the object;
   taking photographs of the object using the condensed light; and
   superposing the photographs of the object to obtain the image of the object.

9. A method for obtaining an image using a selective combination of wavelengths of light, comprising:
- dispersing a light using a prism;
- transmitting the dispersed light through an completely opened openable slit to condense the light that has passed through the openable slit;
- irradiating the light onto an object to measure reflectivities of the light reflected from the object in accordance with positions of portions of the openable slit through which the light passes;
- comparing reflectivity differences between an objective region of the object and a peripheral region of the object;
- selecting positions of portions of the openable slit corresponding to the reflectivity differences indicated as either positive values or negative values;
- opening the portions of the openable slit having the selected positions;
- transmitting the light through the opened portions of the openable slit after dispersing the light using the prism;
- condensing the light that has passed through the opened portions of the openable slit;
- irradiating the condensed light onto the object;
- taking photographs of the object; and
- superposing the photographs of the object to obtain the image of the object.

10. An apparatus for obtaining an image using a selective combination of wavelengths of light, comprising:
- a light source for generating a light;
- dispersing means for dispersing the light to form dispersed light;
- measuring means for measuring reflectivities of the reflected light in accordance with wavelength bands of the light after the light is irradiated onto a object;
- comparing means for comparing reflectivity differences between an object region of the object and a peripheral region of the object;
- selecting means for selecting wavelength bands having the reflectivity differences indicated as either positive values or negative values;
- adjusting means for adjusting the dispersing means to disperse light having the selected wavelength bands only;
- imaging means for taking photographs of the object using the dispersed light; and
- superposing means for superposing the photographs of the object to produce an image of the object.

11. The apparatus as claimed in claim 10, wherein the dispersing means comprises:
- a rotatable prism for dispersing the light generated from the light source; and
- a single slit for transmitting the dispersed light.

12. The apparatus as claimed in claim 10, wherein the dispersing means comprises:
- a prism for dispersing the light generated from the light source; and
- an openable slit for selectively transmitting the dispersed light.

* * * * *